United States Patent [19]
Powell et al.

[11] Patent Number: 5,870,447
[45] Date of Patent: Feb. 9, 1999

[54] METHOD AND APPARATUS FOR GENERATING LOW ENERGY NUCLEAR PARTICLES

[75] Inventors: James R. Powell, Shoreham; Morris Reich, Flushing; Hans Ludewig, Brookhaven; Michael Todosow, Miller Place, all of N.Y.

[73] Assignee: Brookhaven Science Associates, Upton, N.Y.

[21] Appl. No.: 774,669

[22] Filed: Dec. 30, 1996

[51] Int. Cl.[6] ..................................................... G21G 1/10
[52] U.S. Cl. ............................................. 376/194; 376/190
[58] Field of Search ..................................... 376/194, 190, 376/195, 151, 114, 115, 116, 109; 250/390.01, 390.1

[56] References Cited

U.S. PATENT DOCUMENTS

| | | | |
|---|---|---|---|
| 4,112,306 | 9/1978 | Nunan | 376/112 |
| 4,360,495 | 11/1982 | Bauer | 376/151 |
| 4,582,667 | 4/1986 | Bauer | 376/192 |
| 4,666,651 | 5/1987 | Barjon et al. | 376/151 X |
| 4,675,150 | 6/1987 | Russell, Jr. et al. | 376/340 |
| 5,392,319 | 2/1995 | Eggers | 376/194 |

OTHER PUBLICATIONS

Powell, et al., "Target Studies for Accelerator–Based Boron Neutron Capture Therapy", published Jan. 1996 at Brookhaven National Laboratory Library, ten pages.

Lennox, "Proton Linacs for Boron Neuron Capture Therapy", IEEE, Jan. 1993, pp. 1756–1758.

"Abstract Compendium, First International Workshop on Accelerator–Based Sources for Boron Neutron Capture Therapy", Sep. 11–14, 1994, pp. i–74.

Primary Examiner—Charles T. Jordan
Assistant Examiner—M. J. Lattig
Attorney, Agent, or Firm—Margaret C. Bogosian

[57] ABSTRACT

A particle accelerator (12) generates an input particle beam having an initial energy level above a threshold for generating secondary nuclear particles. A thin target (14) is rotated in the path of the input beam for undergoing nuclear reactions to generate the secondary particles and correspondingly decrease energy of the input beam to about the threshold. The target (14) produces low energy secondary particles and is effectively cooled by radiation and conduction. A neutron scatterer (44) and a neutron filter (42) are also used for preferentially degrading the secondary particles into a lower energy range if desired.

25 Claims, 11 Drawing Sheets

METHOD AND APPARATUS FOR GENERATING LOW ENERGY NUCLEAR PARTICLES

This invention was made with Government support under contract number DE-AC02-76CH00016, awarded by the U.S. Department of Energy. The Government has certain rights in the invention.

BACKGROUND OF THE INVENTION

The present invention relates generally to Boron Neutron Capture Therapy, and, more specifically, to the generation of low energy epithermal neutrons therefor.

Energetic epithermal neutron enable penetration to the site of the tumor. Achieving a suitable neutron energy spectrum is very important for effective treatment. If the neutron energy spectrum is too low, their penetration depth into tissue is too small to reach the site of the tumor, if too energetic, the radiation dose to normal tissue is excessive.

BNCT treatment effectiveness is being experimentally investigated using nuclear reactors as the source of neutrons. In the U.S., several patients have been treated at Brookhaven Medical Research Reactor (BMRR), located at Brookhaven National Laboratory. Leakage neutrons from the core are moderated and collimated to produce a suitable beam at the external treatment port.

Reactors have very low neutron utilization efficiencies. Typically, only about $10^{-6}$ of the neutrons that are released in the core are actually available at the treatment port. This is a result of the inherent dimensional constraints imposed by criticality, and the relatively long distances required to slowdown high energy neutrons using conventional moderators. Gamma shielding requirements are also a contributing factor. As a result, in the BMRR, for example, the treatment port is located at a distance of 177 centimeters from the center of the core. In the MURR (Missouri University Research Reactor) BNCT design, the treatment port is 310 centimeters from the center of the core.

As a result of this very low neutron utilization efficiency, a reactor-based neutron source for BNCT requires high operating power, on the order of several megawatts, and is a large, very expensive, one of a kind facility with a limited capability to treat large numbers of patients.

In contrast, accelerator-based neutron sources for BNCT appear to have very attractive features, as compared to reactor based neutron sources: much lower facility cost, greatly reduced residual radioactivity, much lower operating power, greatly reduced safety concerns, and a better neutron energy spectrum for treatment.

Compared to reactor-based BNCT facilities, accelerator-based facilities could be located at a much larger number of sites, enabling many more patients to be treated.

Various concepts for accelerator-based BNCT systems have been proposed in which a particle beam interacts with a target to generate neutrons. Depending on the particular concept, the nuclear reaction involved can be a (p, n) reaction, a $H^3$ (d, n) $He^4$ reaction, and so forth.

A particularly promising approach is the proton beam—lithium target concept, in which a low energy proton beam (about 2 MeV) strikes a lithium target, generating neutrons by the (p, n) reaction. Its attractive features include:

Relatively high neutron yield per proton (about $10^{-4}$);

Low maximum energy of generated neutrons;

Simple, low energy proton accelerator;

Simple, readily cooled target; and

Minimal shielding and residual radioactivity.

A number of design studies of the proton beam—lithium target concept have been carried out, including the use of a radio frequency quadrupole (RFQ) linac to accelerate protons to strike a lithium target with an energy above the 1.8 MeV production threshold for the $^7Li(p,n)^7$ Be reaction. These previous studies, while they show that the concept is feasible, end up requiring the proton beam current to be in the range of 50–100 milliamps in order to achieve adequate neutron flux at the treatment port.

Accelerators for producing beam currents at this level are technically challenging, and costly as well. In addition, the target generated neutron energy spectrum typically has a substantial fast neutron component that would cause objectionable radiation dose in normal, noncancerous tissue. The gamma dose to normal tissue is also significant. Finally, cooling of the accelerator targets at the required power levels is difficult.

In these previous designs, the high energy neutrons generated by the target/proton interactions are degraded to the treatment regime, i.e., on the order of 10 keV in energy, by scattering collisions with a suitable moderator (e.g., BeO, $Al_2O_3$, etc) With such materials, to achieve the requisite energy degradation needed for a useful energy spectrum, the target must be located at some distance from the patient treatment zone. Consequently, for such systems, the neutron utilization efficiency, that is, the ratio of the rate at which useful neutrons are introduced into the patient treatment zone to the rate at which neutrons are generated by proton/target interactions, is typically in the range of 0.1 to 0.5 percent. That is, only $\frac{1}{1000}$th to the $\frac{1}{200}$th of the neutrons in the target actually are available for use in the patient treatment zone.

However, such efficiencies are still orders of magnitude greater than those achieved by medical reactor systems. Because of the inherently much greater distance between the neutron generating reactor core and the patient treatment zone, due to the inherent dimensional constraints imposed by criticality and the shielding requirements, the neutron utilization efficiency for medical reactors is on the order of $10^{-6}$. Thus for medical reactors, only about one millionth of the generated neutrons actually are available for use in the patient treatment zone.

The accelerator-based proton beam-lithium target approach still has unsolved critical problems including high proton beam current requirements, excess energy neutrons, and cooling of the lithium target which has a low melting temperature. An alternate target being considered is beryllium which has a higher melting point than lithium, is easier to cool, and has been used successfully in clinical fast neutron therapy facilities. The neutron production threshold for protons impinging on a beryllium target is 2.2 MeV and the yield becomes comparable to a lithium target yield at about 4 MeV. However, using 4 MeV protons and a beryllium target produces even more energetic neutrons than the system described above, and therefore requires suitable moderation.

Accordingly, it is desirable to generate low energy epithermal neutrons for BNCT in an accelerator-based apparatus having relatively low proton beam current and suitable cooling of the target.

SUMMARY OF THE INVENTION

A particle accelerator generates an input particle beam having an initial energy level above a threshold for generating secondary nuclear particles. A thin target is rotated in the path of the input beam for undergoing nuclear reactions to generate the secondary particles and correspondingly decrease energy of the input beam to about the threshold. The target produces low energy secondary particles and is effectively cooled by radiation and conduction. A neutron scatterer and a neutron filter are also used for preferentially degrading the secondary particles into a lower energy range if desired.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DESCRIPTION OF THE PREFERRED EMBODIMENT(S)

The present invention includes in a preferred embodiment an improved accelerator target, termed DISCOS (Discs Incorporating Sector Configured Orbiting Sources). DISCOS may be used for generating low energy epithermal neutrons for BNCT applications. And, DISCOS may be used for other applications such as spallation targets. In a preferred embodiment, DISCOS is applied to a system in which a proton beam impacts a lithium target to generate neutrons by the (p, n) reaction. However, the DISCOS could also be applied in other accelerator applications employing different particles and different targets.

DISCOS uses one or more ultra thin (i.e., on the order of a few microns in thickness) lithium targets that are impacted by the proton beam. The targets would be thin enough that the proton beam loses only a small portion of its energy, at most a few tens of keV, in its passage through an individual lithium target.

After impacting the target, the protons in the beam may be re-accelerated to bring their energy back up to the initial value. This could be done by recirculating the beam and directing the beam back through a particle accelerator that would make up the energy lost in each repetitive pass through the lithium target. Alternatively, a multiple set of thin lithium targets can be used, within a DC electric field. The energy loss experienced by the protons in passing through a given target would then be compensated for by the energy gained in the DC field as the protons traveled to the next lithium target.

DISCOS enables the efficient generation of low energy epithermal neutrons from lithium targets. The proton beam energy can be held just above the threshold value for neutron production, so that the output neutrons are born with low energies. If a single fixed target were used, however, the resultant neutron yield, i.e., neutrons generated per beam proton, would be very low, and the energy efficiency, i.e., neutrons per MeV of proton input energy, very small. By re-accelerating the protons each time they pass through a thin lithium target, both the energy yield and energy efficiency can be increased by a large factor, on the order of 10 to 100 times, depending on design, while still maintaining the output of low energy neutrons.

To achieve comparable neutron yields per proton and energy efficiency with a single fixed target, the initial energy of the proton beam would have to be far above the threshold value for neutron production, with the result that the output neutrons would have much greater average energy and a much higher maximum energy.

Figure 1:
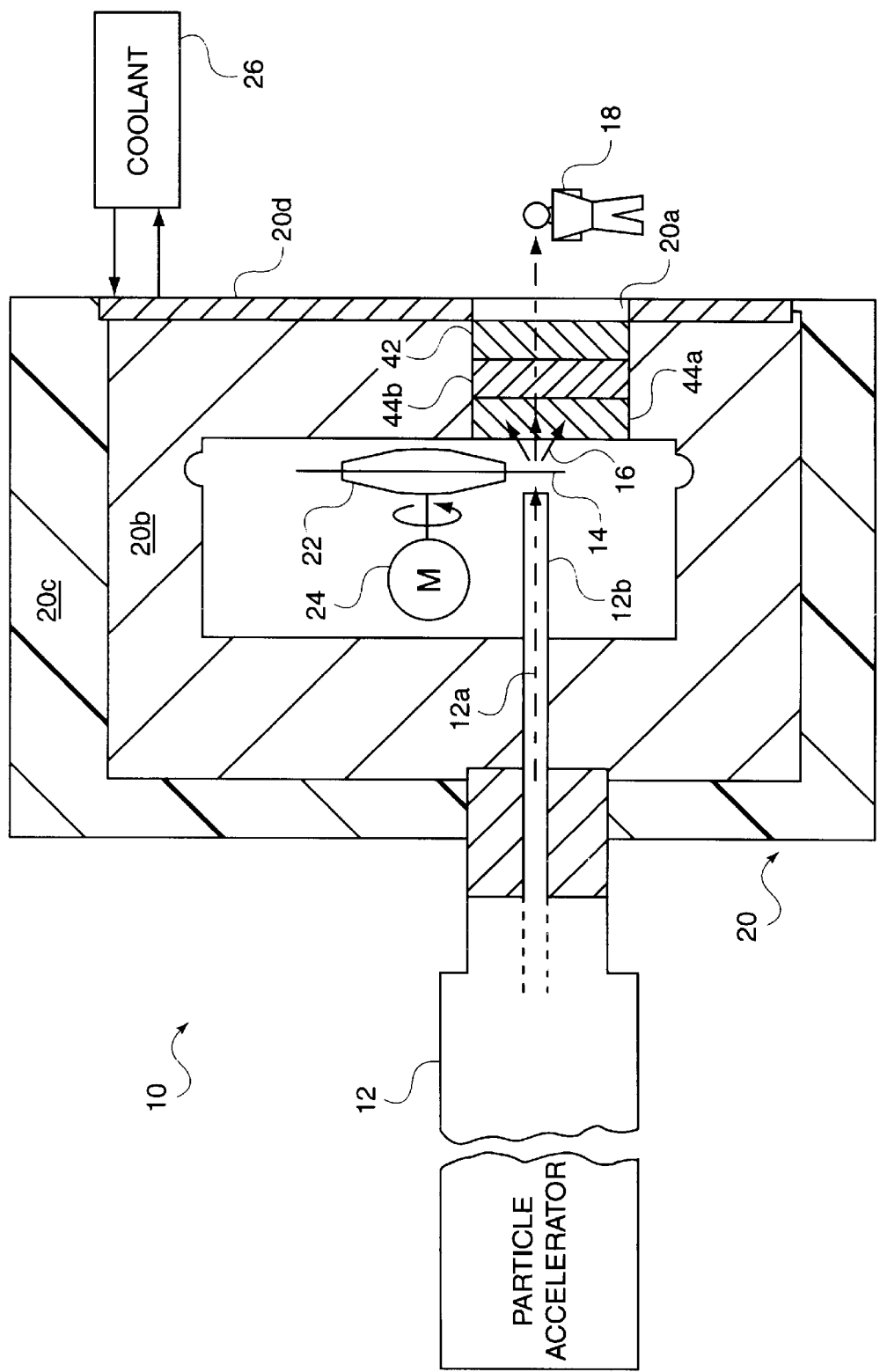
FIG. 1 is a schematic representation of an apparatus for generating low energy secondary nuclear particles from an accelerated particle beam in accordance with an exemplary embodiment of the present invention.

Illustrated in FIG. 1 is an exemplary apparatus 10 for generating low energy nuclear particles using the DISCOS approach. A particle accelerator 12 produces a primary particle beam 12a which is directed at a rotary target 14 which undergoes nuclear reactions for generating secondary nuclear particles in the form of an output beam 16 all within a suitably high vacuum. The accelerator 12 may take any conventional form for producing a suitable input particle beam 12a to the target 14, formed of a suitable material. For example, the accelerator 12 may be an RFQ linac proton accelerator for producing a proton beam 12a, with the target 14 being formed of preferably lithium or beryllium for generating secondary particles in the form of neutrons preferably at a relatively low energy in the epithermal energy range.

In the exemplary embodiment illustrated in FIG. 1, the apparatus 10 is configured for use in performing boron neutron capture therapy (BNCT) in a patient 18. It is desirable to produce the neutron beam 16 with suitably low energy neutrons in the epithermal range for maximizing destruction of cancer cells in the patient 18 while minimizing damage to normal tissue therein. A preferred range of therapeutic neutrons is about 1 eV–10 keV. However, epithermal neutrons may have energies up to about 100 keV which are undesirably too energetic for use in the neutron capture therapy. It is therefore desirable to more directly produce the output neutron beam 16 with epithermal neutron energies in the desired low range.

The particle accelerator 12 illustrated in FIG. 1 is suitably attached to a chamber 20 in which is suitably mounted the target 14. The accelerator 12 includes a suitable proton beam tube 12b extending through the chamber 20 and adjacent to the target 14 for directing the proton beam 12a at the target 14 for undergoing nuclear reactions therein. Since neutrons and radiation are emitted from the target 14 during operation, the chamber 20 includes suitable safety shields for confining the nuclear reactions, with a suitable treatment port 20a providing egress from the chamber 20 for the neutron beam 16 to reach the patient 18.

Preferably, a first chamber shield 20b surrounds the target 14 in most part to provide a suitable neutron reflector using materials such as lead or titanium with boron, for example. A second chamber shield 20c surrounds the first shield 20b in most part to provide a suitable neutron moderator and absorber and may be formed of polyethylene and boron, for example. A third shield 20d surrounds the treatment port 20a along the downbeam side of the first shield 20b for stopping undesirable low energy neutron radiation from the chamber 20, and may be in the exemplary form of lithium (Li) or $B_4C$.

The neutron yield in the output beam 16 from the target 14 is directly related to the energy of the incident input proton beam 12a. Higher neutron yield may be obtained by using higher proton energy. However, as proton energy increases, the average energy of the output neutrons also increases above the desirable epithermal neutron energy range for BNCT. It is therefore desirable to produce the output neutron beam 16 with relatively low energy in the epithermal range with a suitable neutron yield effective in conducting BNCT.

In accordance with the present invention, the target 14 is made ultrathin, and the proton beam energy is held just above the threshold value for neutron production so that the neutrons in the output beam 16 are born with suitably low epithermal energy. The target 14 is therefore sufficiently thin so that the excess energy in the proton beam 12a above the required threshold value is only so much as is needed to produce epithermal neutrons from the target 14, with the energy in the proton beam 12a then dropping to about the threshold energy level.

For example, the target material may be lithium or beryllium for undergoing (p,n) nuclear reactions for producing neutrons from the incident proton beam. The threshold energy level of a proton beam with a lithium target is about 1.88 MeV, and with a beryllium target is about 2.2 MeV. A lithium target is preferred in view of the lower threshold energy required for thereby producing lower energy neutrons, but lithium has a lower melting temperature than beryllium and would melt at the elevated temperatures involved during operation which may be on the order of about 1000° K.

However, maximum performance for either target may be obtained by making the target suitably thin and correspondingly increasing the energy of the proton beam slightly above the threshold so that the target will undergo nuclear reactions to generate the neutrons and correspondingly decrease the energy of the proton beam to about the threshold. Accordingly, the initial energy level of the input particle beam is only just above or closely above the threshold level for generating the neutrons, and will decrease to about the threshold level upon generation of the neutrons in the target. In this way minimum input energy is received by the target for generating neutrons with minimally low energy levels at the inception.

In accordance with the present invention, the target 14 may be solid, or liquid, or both and suitably thin on the order of about one micron, for example. Depending upon the energy and the type of input particle beam, as well as the target material and thickness, the energy lost by the particles in their transport through the thin target may be in the range of a few keV to a few tens of keV. For example, protons slightly above the 1.88 MeV threshold energy (p,n) reactions on lithium will lose about 8 keV per micron of lithium thickness.

Accordingly, the input proton beam 12a may have an initial energy level of about 1.9 MeV so that the 8 keV energy loss in the thin lithium target will reduce the energy of the proton beam down to about the threshold value. The resultant neutrons are therefore born with as little energy therein as possible. And the low power requirement for the particle accelerator 12 is presently available using conventional proton beam accelerators without the need for developing substantially higher energy proton beam accelerators.

The energy of the particle beam 12a is nevertheless sufficient to cause considerable heating of the target 14 and operation at relatively high temperature on the order of about 1000° K. Cooling of the target 14 is therefore a fundamental problem in effecting a practical accelerator-based BNCT system.

In accordance with the present invention, suitable means are provided for rotating the target 14 at a suitable rotary speed, such as 10,000 rpm for example, for distributing and dispersing the heat load received from the particle beam 12a to promote conduction and radiation heat transfer for cooling the target 14. As shown schematically in FIG. 1, the target 14 is suitably fixedly joined to the perimeter or rim of an annular disk 22, and a suitable motor 24 is fixedly joined thereto for rotating the disk and in turn the target 14 for spreading the input heat load around the target 14 and allowing conduction and radiation heat transfer inside the chamber 20.

The target 14 is maintained under a suitably high level of vacuum in the chamber 20 which prevents convection heat transfer. However, the heat load from the incident proton beam 12a on the target 14 spreads by conduction through the target 14 and increases the effective area of radiation thereof on the inside of the chamber 20. The chamber 20 may further include suitable means 26 for cooling the chamber due to the energy input from the proton beam 12a. The cooling means 26 may take any conventional form and include suitable supply and return conduits distributed throughout the chamber 20 for absorbing the heat therein in a suitable coolant, such as water, which is then recirculated through a suitable heat exchanger.

Figure 2:
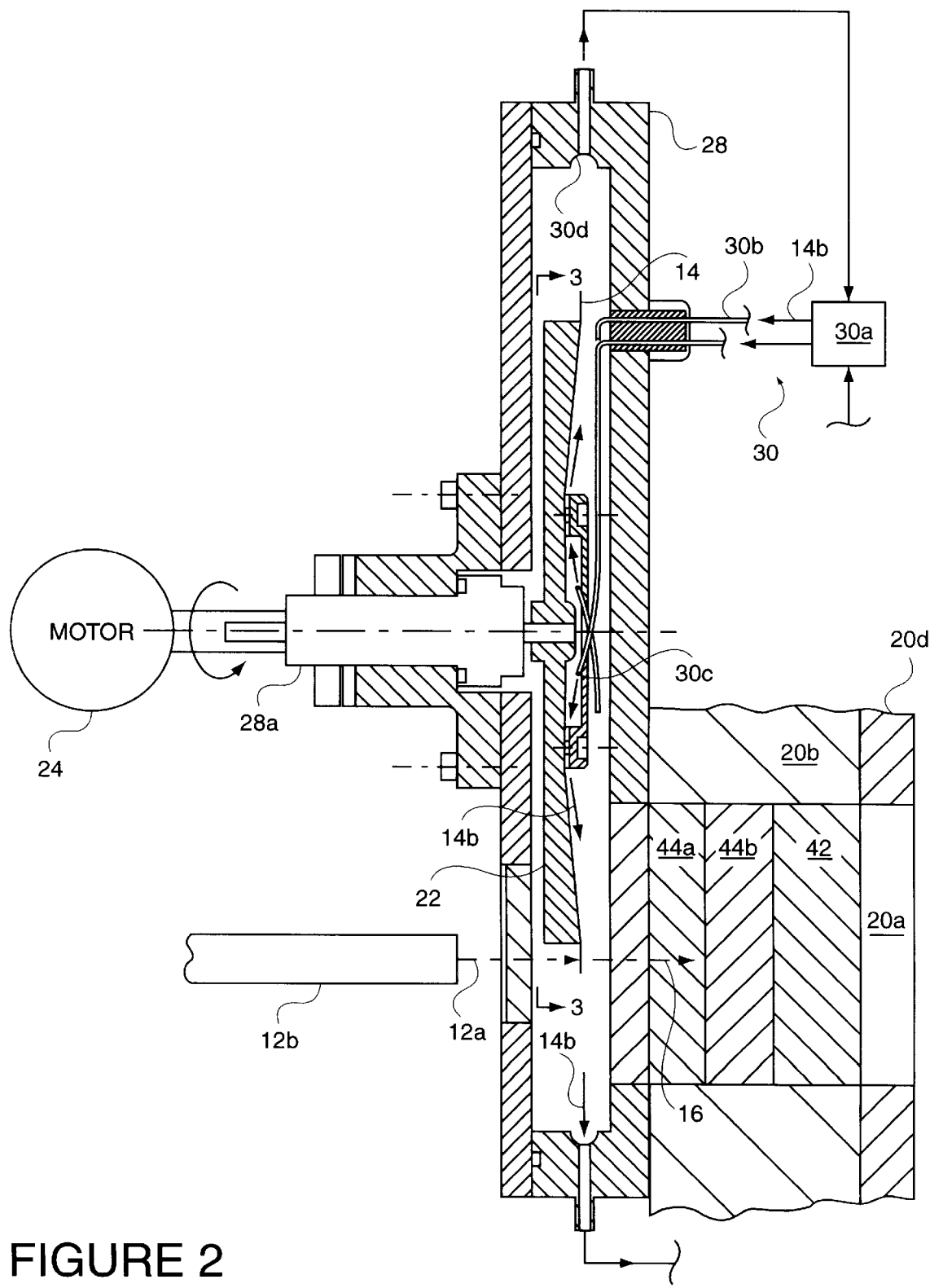
FIG. 2 is a partly sectional, elevational view through a disk mounted rotary target in accordance with an exemplary embodiment of the present invention for use in the apparatus illustrated in FIG. 1 for generating low energy secondary particles from the particle beam.
Figure 3:
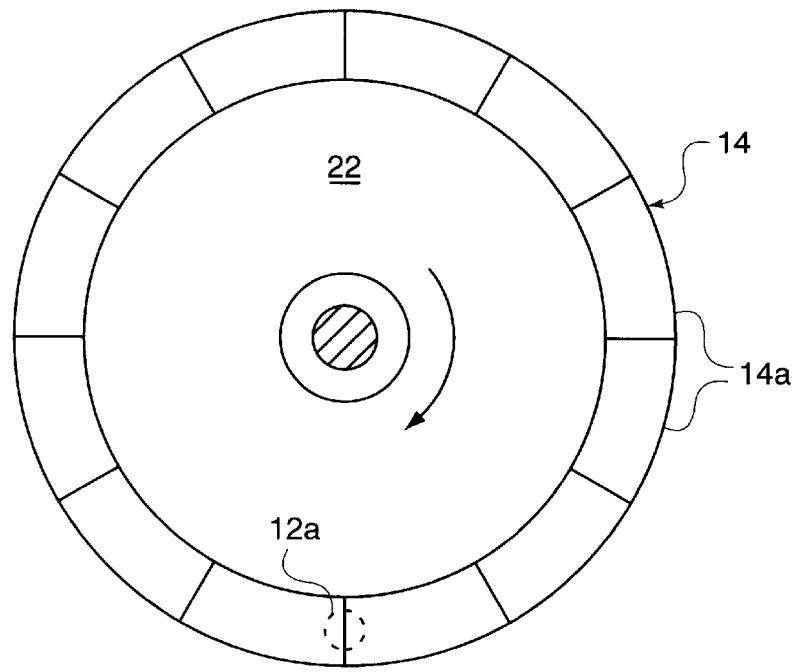
FIG. 3 is an end view of the rotor disk and target illustrated in FIG. 2 and taken along line 3—3.

An exemplary embodiment of the disk mounted target 14 is illustrated in FIGS. 2 and 3. In this embodiment, the target 14 is a solid, ultrathin foil on the order of about one micron thick, and is circumferentially sectored into a plurality of circumferentially adjoining arcuate foils segments 14a suitably fixedly joined to the perimeter of the disk 22 to form a complete ring. The disk 22 is preferably mounted in a stationary housing 28 inside the chamber 20, and is maintained at a suitable level of vacuum for promoting the generation of the neutron beam 16 upon impact of the proton beam 12a with the target 14.

A suitable rotary vacuum seal 28a extends from the disk 22 inside the housing 28 to outside the housing 28 and is attached to the motor 24 for rotating the disk 22 at a suitable rotary speed of about 10,000 rpm for example. As the disk 22 rotates, the proton beam 12a circumferentially traverses the foil segments 14a and thereby spreads the heat input thereto. Conduction disperses the heat throughout the target 14, and radiation disperses the heat into the housing 28 and in turn into the chamber 20 for maintaining the target 14 at an acceptable temperature during operation. The small thickness of the ultrathin target 14 improves the heat conduction therethrough and heat dissipation, and minimizes residual heat in the target 14.

The target 14 may be a continuous annulus, or is preferably circumferentially segmented as shown for eliminating hoop stresses therein. This can enable much faster rotation, and more reliable, longer life operation of the target 14. The operating temperature of the target 14 is nevertheless relatively high and most likely greater than the melting temperature of lithium. Accordingly, in the solid embodiment of the target 14, beryllium may be used, whereas a lithium target may be used in liquid form with or without a backing foil, such as beryllium, to hold the lithium film. However, foil targets produce parasitic losses of the proton beam, and thus increase the proton current needed to achieve the given neutron production rate.

Figure 4:
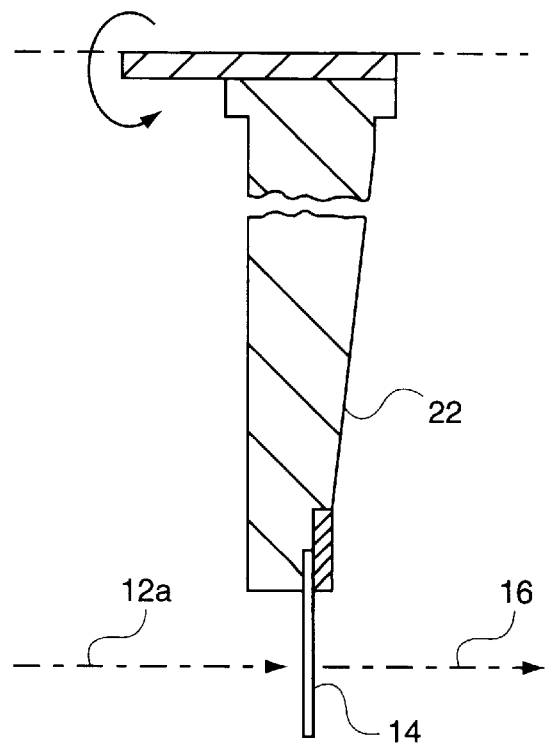
FIG. 4 is a partly sectional, elevational view of the lower portion of the rotor disk illustrated in FIG. 2 having a solid foil target attached to the perimeter of the disk in accordance with an exemplary embodiment of the present invention.

The foil parasitic losses may be minimized by using a foil that is made of a low Z material, and as thin as possible. Beryllium foil is a preferred material since it has a low Z value of about 4 and may be manufactured as a thin metallic foil on the order of about one micron thick. Beryllium generates some neutrons when impacted by a proton beam although not as much as a corresponding lithium target. FIG. 4 illustrates the use of only a solid, beryllium target 14 in sectored form suitably fixedly attached or clamped to the rim of the disk 22 for receiving the proton beam 12a in generating the output neutron beam 16.

In the preferred embodiment illustrated in FIG. 2, lithium is the target material and is a molten liquid at the operating temperatures involved. Accordingly, the liquid lithium must be suitably handled for developing a target either alone or with a suitable backing foil.

In the exemplary embodiment illustrated in FIG. 2, means 30 are provided for channeling liquid lithium 14b to the perimeter of the disk 22 for centrifugally forming a liquid film target 14 for receiving the proton beam 12a. The lithium channeling means 30 includes a suitable lithium supply and pump 30a joined in flow communication to a plurality of liquid feed lines 30b which extend through the housing 28 and adjacent to the rotating disk 22 near its hub. The ends of feedlines 30b define spray nozzles 30c which eject the lithium 14b against the outer surface of the disk 22 near its hub.

The liquid lithium 14b adheres to the surface of the disk 22 and spreads circumferentially as it flows radially outwardly due to centrifugal force. The lithium 14b forms an annular sheet as it spins radially outwardly from the perimeter of the disk 22. The liquid sheet defines the target 14 and has suitably small lithium droplets which receive the proton beam 12a to generate the secondary neutron particles. The outer circumference of the housing 28 includes an annular trough 30d which collects the lithium spray from the rotating disk 22 and returns it to the lithium supply 30a for recirculation.

Figure 5:
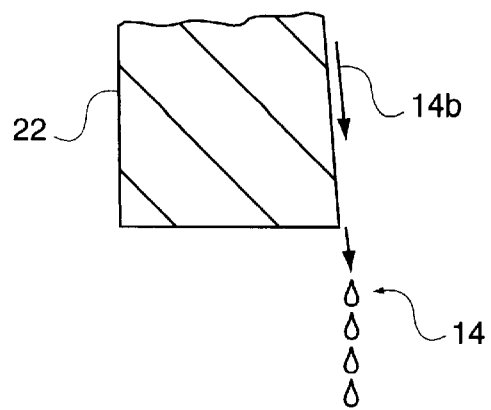
FIG. 5 is a partly sectional view of the radially outer tip region of the rotor illustrated in FIG. 2 in accordance with another embodiment of the present invention having solely a liquid target dispersing radially outwardly therefrom.

The lithium channeling means 30 may take any suitable form for providing liquid lithium either along an outer surface of the disk 22 or internally therethrough so that the lithium may be spun by centrifugal force at the perimeter of the disk 22 to develop a relatively thin lithium spray radially outwardly therefrom for defining the target 14. The lithium spray droplets should be as small as possible and on the order of about one micron in diameter to effect the ultrathin target described above for directly producing low energy neutrons therefrom upon bombardment by the proton beam 12a. FIG. 5 illustrates an enlarged view of the target 14 defined by a liquid lithium sheet created by spinning the disk 22.

Figure 6:
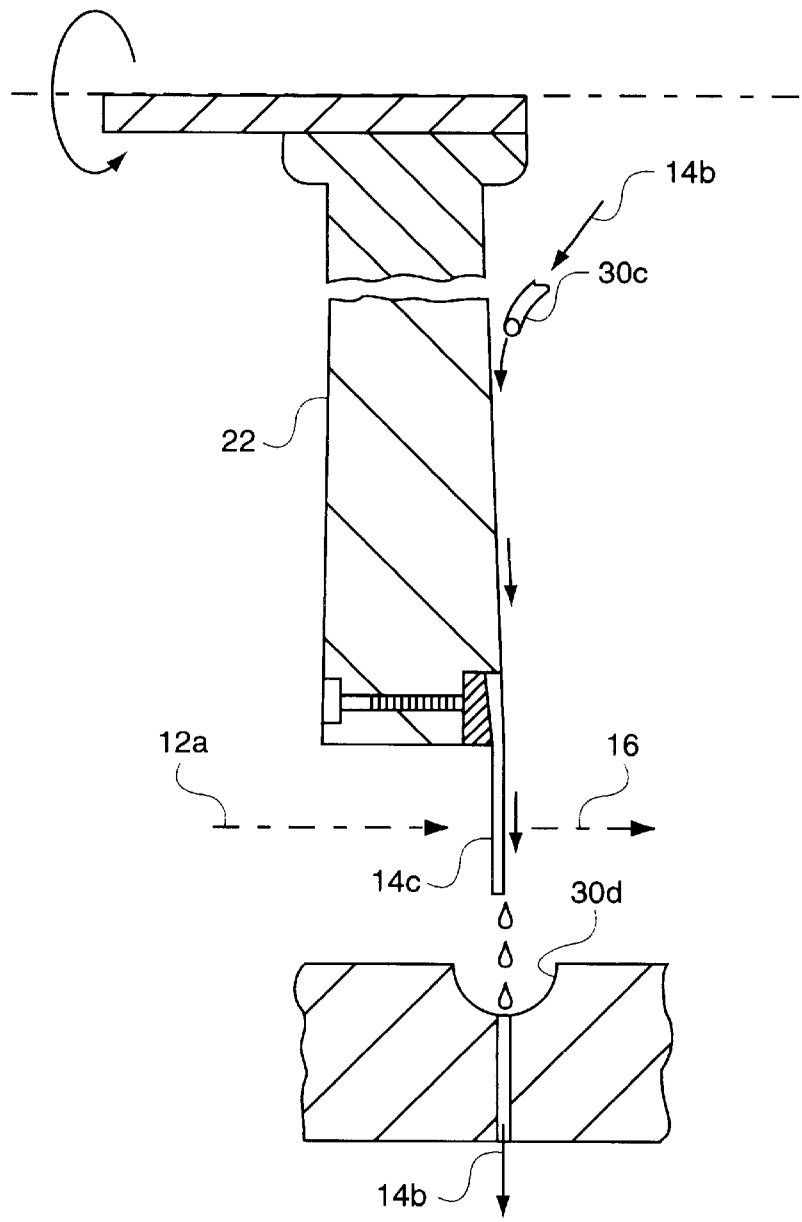
FIG. 6 is an elevational sectional view like FIG. 4 of a rotor disk having a thin foil perimeter target and liquid target flow there over in accordance with another embodiment of the present invention.

FIG. 6 illustrates an alternate embodiment wherein the liquid lithium 14b is channeled at the perimeter of the disk 22 by a thin backing foil 14c for controlling the sheeting action of the liquid lithium 14b as well as for providing cooling. The backing foil 14c may be a thin beryllium foil defining the target itself, with the lithium 14b being used for cooling the foil, in which case neutrons are generated both in the beryllium backing foil 14c and the lithium sheet. Or, the backing foil 14c may be secondary to neutron production and is provided primarily for supporting the liquid lithium 14b at the disk perimeter. In this way, a more continuous sheet of the liquid lithium 14b may be defined at the perimeter of the disk 22 and again is relatively thin on the order of about one micron for passing therethrough the proton beam 12a for generating the secondary neutrons 16 therefrom. The same lithium channeling means 30 may be used in the embodiment illustrated in FIG. 6 for channeling the liquid to the disk perimeter for centrifugally forming the liquid film on the backing foil segments 14c for receiving the input proton beam 12a.

Figure 7:
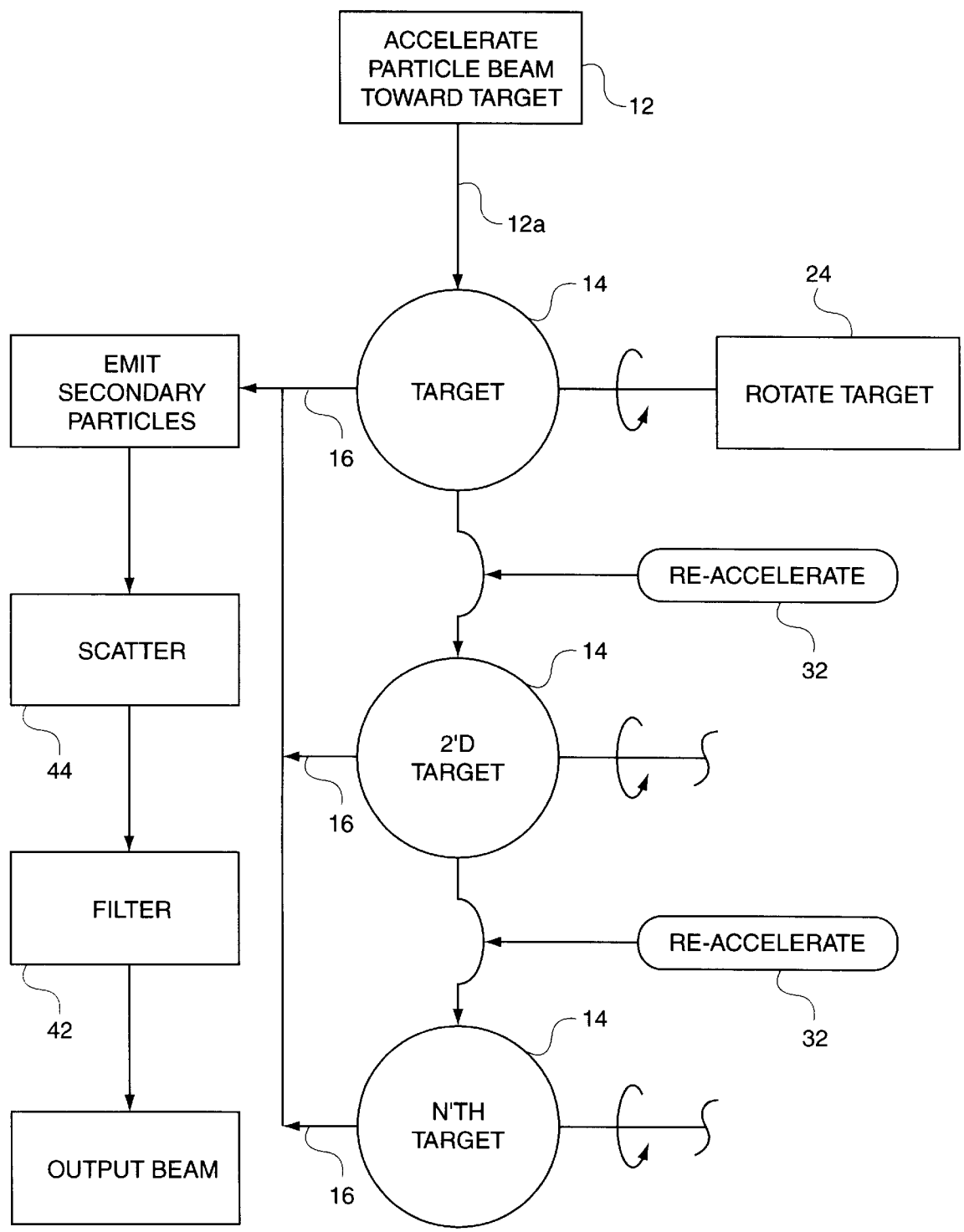
FIG. 7 is a flowchart representation of a method of generating low energy secondary nuclear particles in accordance with an exemplary embodiment of the present invention.

FIG. 7 illustrates in flowchart form exemplary methods of practicing the invention. As indicated above, the particle accelerator 12 is used for generating the input particle beam 12a at an energy level just above the threshold level for a particular target for generating the secondary neutron particles 16. The motor 24 rotates the target 14 as described above for promoting heat dissipation and ensuring an effective useful life of the target 14 during operation.

In order to obtain an acceptable neutron yield using a single, ultrathin target 14 described above, the proton beam current would be undesirably high on the order of about 200 mA. In accordance with the present invention, the proton beam current may be substantially reduced to only a few milliamps for an effective neutron yield by recirculating and reaccelerating the proton beam through the same or multiple targets for collectively producing the secondary neutrons therefrom. FIG. 7 illustrates the use of a plurality of identical targets 14 which in turn receive the proton beam 12a which is then reaccelerated between the targets back to the initial energy level.

Figure 8:
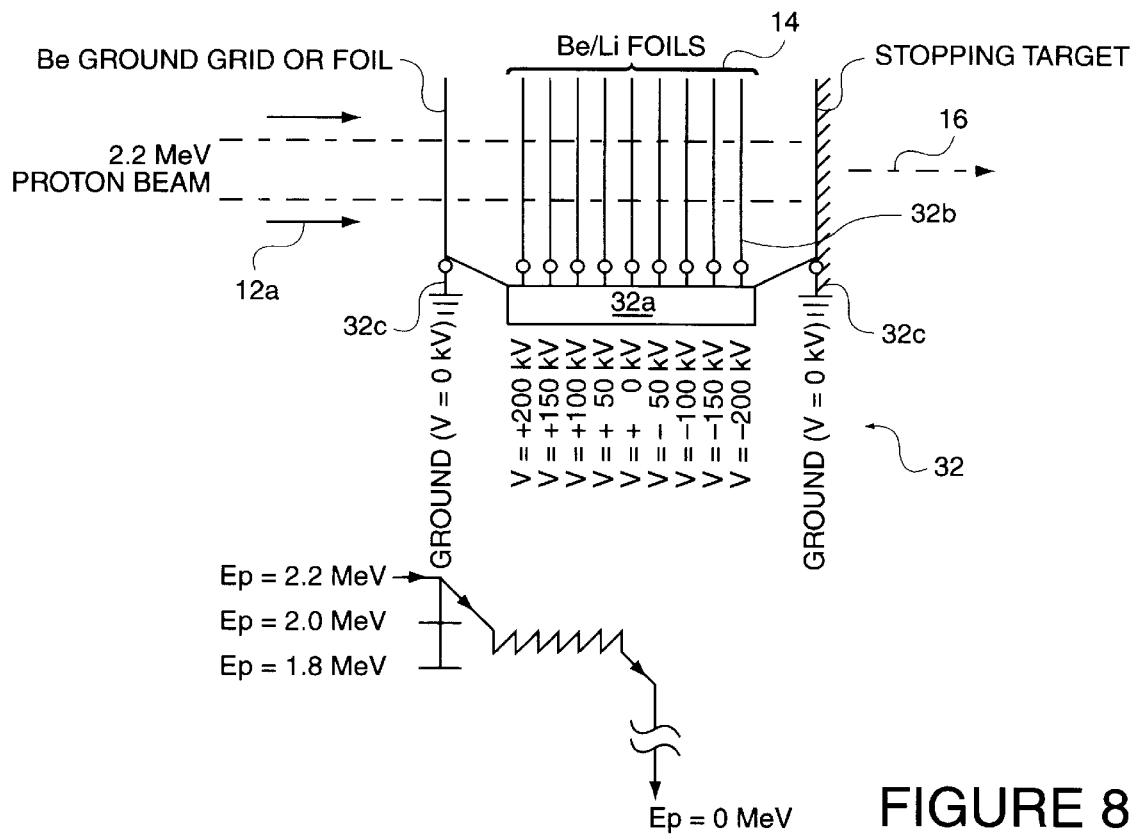
FIG. 8 is a schematic representation of multiple rotary targets with a DC voltage potential there across for reaccelerating the input particle beam between successive targets for generating the low energy secondary particles.
Figure 9:
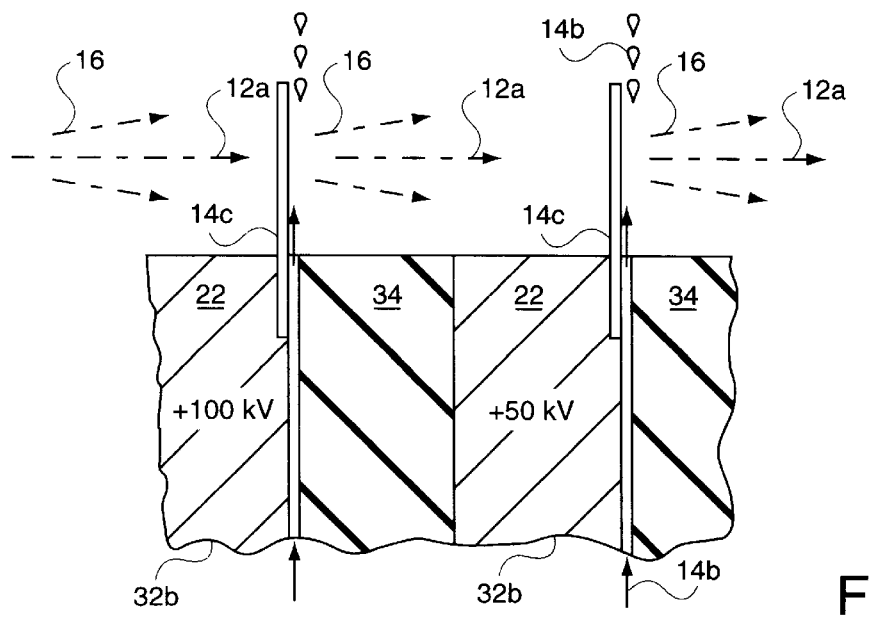
FIG. 9 is a partly sectional, elevational view of a portion of adjoining rotary targets of FIG. 8 having liquid covered foil targets at different voltage potentials.

A schematic representation of a multi-target embodiment is illustrated in a preferred form in FIGS. 8 and 9. In this embodiment, a plurality of axially spaced apart targets 14 are joined coaxially to the motor 24 for simultaneous rotation. The targets 14 may take any suitable form as described above, either solid or liquid, or both. As shown in FIGS. 8 and 9, the thin beryllium backing foil 14c is used with the liquid lithium 14b suitably channeled radially outwardly thereover to define the respective targets which receive in turn the proton beam 12a for generating the secondary neutrons 16. The proton beam 12a is therefore directed in turn through the targets to generate the neutrons 16, which correspondingly decreases energy of the proton beam 12a at each of the targets to about the threshold value.

In this exemplary embodiment, the proton beam threshold energy level (Ep) is about 1.8 MeV, and the initial energy of the proton beam just prior to each of the succeeding targets 14 is slightly above the threshold value, and is about 2.0 MeV for example. Each of the targets 14 is again relatively thin on the order of one micron so that the energy loss in the proton beam through each target reduces the proton beam energy to about the threshold for directly generating low energy epithermal neutrons from the targets 14. Since the proton beam energy is diminished upon traversing each target, it is repetitively reaccelerated between succeeding ones of the targets 14 up to about the original or initial energy level, e.g., 2.0 MeV, prior to undergoing the nuclear reactions in each target for generating the secondary neutrons.

By using multiple thin targets in sequence, on the order of thirty or more targets, several hundred keV of reacceleration energy can be added to the particle beam 12a, while simultaneously keeping the average energy of the particle beam 12a just a few keV above the threshold. This significantly improves the yield of the low energy epithermal neutrons while minimizing the required current of the proton beam 12a.

The proton beam 12a may be reaccelerated from target to target in any suitable manner such as by diverting the proton beam 12a through a suitable magnetic lens for reacceleration in a remote radio frequency (rf) cell suitably configured therefor.

In a preferred embodiment as illustrated in FIGS. 8 and 9, means 32 are provided for repetitively reaccelerating the proton beam 12a between succeeding ones of the targets 14 to about the initial energy level prior to undergoing the nuclear reactions thereat. The reaccelerating means 32 illustrated are effective for applying a direct current (DC) voltage potential across the targets 14 to reaccelerate the particle beam 12a therebetween. The reaccelerating means 32 preferably applies the voltage potential in decreasing incremental steps at each of the target 14 in turn.

In the exemplary embodiment illustrated in FIGS. 8 and 9, the recirculating means 32 includes a suitable DC power supply 32a operatively joined to a plurality of biasing electrodes 32b maintained at different DC voltage potentials bridging the targets 14 to reaccelerate the proton beam 12a therebetween. As shown in the exemplary embodiment of FIG. 9, the individual disks 22 may be formed of a suitable electrically conducting metal with suitable electrical insulators 34 stacked therebetween for isolating each of the disks 22 from each other. The power supply 32 is suitably electrically joined to each of the disks 22 for defining the corresponding electrodes 32b biased at a suitable DC voltage. Slip rings and conducting circuits may be provided between the stationary power supply 32a and the rotating disks 22 in any conventional and suitable manner for biasing each of the disks 22, and in turn the electrically conducting target foils 14c attached thereto.

In the exemplary embodiment where the input particle beam 12a is a proton beam, increasing negative voltage from target to target in turn is required for reaccelerating the proton beam between the several targets 14. The magnitude of the applied DC voltage is correspondingly selected for returning the proton beam 12a to about its initial energy, of about 2.0 MeV for example, at each of the targets 14. This may be accomplished by providing a 50 kV DC voltage step from target to target. The greater the number of targets 14 used in series, the greater the overall DC voltage drop thereacross is required. The voltage potential may increase in magnitude negatively from the first to the last of the targets 14 in turn which would create substantial electrical insulating problems for the high voltages involved.

However, in the preferred embodiment illustrated in FIG. 8, a pair of ground electrodes 32c having zero voltage potential bridges all of the targets 14, with the first ground electrode 32c being in the preferred form of a thin target foil, such as beryllium, suitably grounded to the power supply 32a. The axially opposite ground electrode 32c may have any suitable composition, such as beryllium, for also providing an effective stop for the proton beam 12a when it finishes its travel to the targets 14.

The individual targets 14 are positioned in turn axially between the pair of ground electrodes 32c, with the first target 14 having a maximum positive DC voltage, and the last target 14 having a minimum negative DC voltage, plus 200 kV and minus 200 kV, respectively, for example. The targets 14 therebetween suitably decrease in voltage potential in equal increments, of about 50 kV for example for the nine targets 14 illustrated in the exemplary embodiment. As more targets 14 are used, the incremental DC voltage should maintain a suitably high value for effecting the acceleration of the proton beam 12a, with the maximum and minimum voltages at the first and last targets 14 having suitably large values.

The first ground foil 32c allows the first target 14 to be referenced to a positive DC voltage which therefore allows the electrical configuration to be practically implemented using a power supply 32a with equal positive and negative voltage potentials in a symmetrical fashion. The overall voltage drop of the exemplary power supply 32a illustrated in FIG. 8 is 400 kV which is more practically implemented by using a power supply having positive and negative 200 kV potentials for achieving this total.

In operation, the proton beam 12a is provided with a higher preliminary energy of about 2.2 MeV for example, which decreases to about 2.0 MeV upon traversing the first ground electrode 32c which is suitably thin for achieving this energy drop. The particle beam 12a then has an initial energy of 2.0 MeV for impacting the first target 14 with the energy in the proton beam then decreasing to about the threshold value. The 50 kV potential between each of the targets 14 is effective for reaccelerating the proton beam up to its initial 2.0 MeV value prior to impacting each of the subsequent targets 14. In this way a substantial increase in neutron yield may be achieved with relatively low proton beam current while minimizing the energy spectrum of the secondary neutrons generated in a more desirable epithermal energy range.

In the preferred embodiment, the targets 14 are preferably lithium films 14b having a thickness of less than about two microns, with a corresponding beryllium backing foil 14c if desired, and the threshold energy of the proton beam 12a is about 1.88 MeV for generating neutrons in the (p,n) reactions in lithium and beryllium. Although the preliminary energy of the proton beam 12a is about 2.2 MeV in the exemplary embodiment illustrated in FIG. 8, the initial energy level of the proton beam 12a impacting the first target 14 is preferably less than about 2.2 MeV and suitably just above the threshold value for directly producing minimum energy epithermal neutrons less than about 100 keV for more closely achieving the desirable epithermal energy range of 1 eV–10 keV for boron neutron capture therapy.

Figure 10:
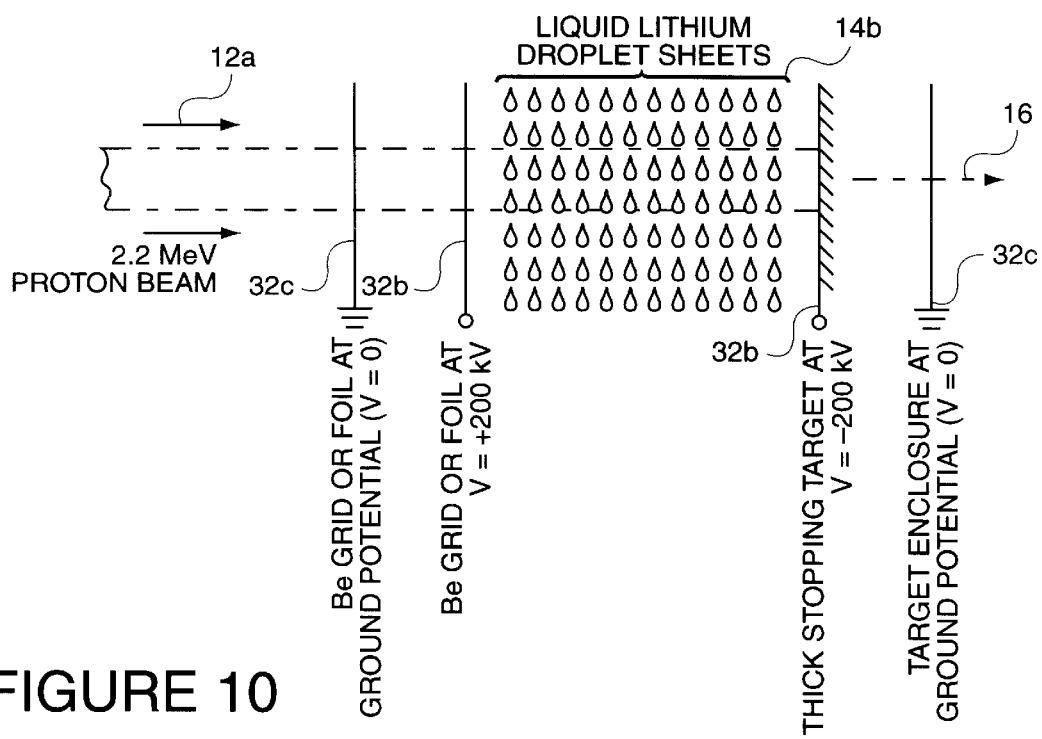
FIG. 10 is a schematic representation analogous to FIG. 8 illustrating multiple rotary targets in the form of liquid sheets having a voltage potential there across for reaccelerating the input particle beam between the sheets.
Figure 11:
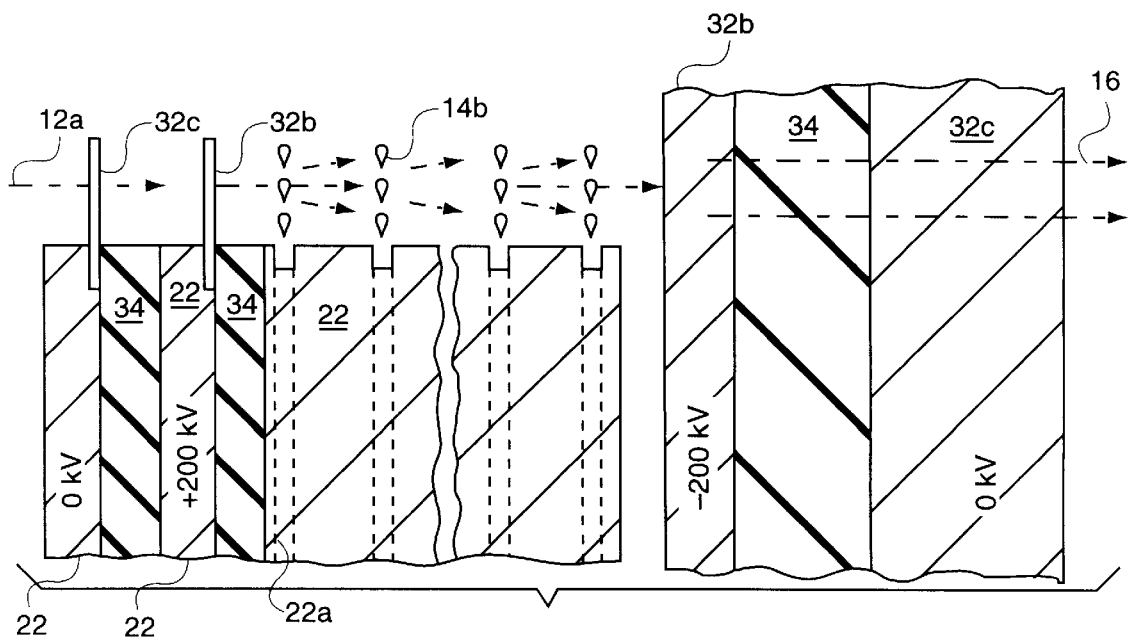
FIG. 11 is a partly sectional, elevational view of a portion of the apparatus shown in FIG. 10 illustrating rotary voltage biasing foils and adjoining disks for centrifugally dispersing the liquid target in a plurality of axially spaced apart sheets.

FIGS. 10 and 11 illustrate schematically another embodiment of the present invention similar to the FIG. 8–9 embodiment wherein the targets are solely in the form of a plurality of axially spaced apart liquid lithium droplet sheets 14b without backing foils. The liquid lithium sheets may be formed using any suitable arrangement. For example, materials with very fine pores, e.g., on the order of one micron in diameter, are commercially available. These materials are typically used as filters, and are made of a wide variety of metallic and non-metallic substances such as stainless steel and $Al_2O_3$, respectively. They may be used in the disk 22 for generating sheets of ultra fine droplets. Stacked metallic porous disks may be separated by non-porous, non-metallic electrically insulating spacer disks. Or, porous non-metallic disks may be used with suitable internal ducts.

As illustrated in FIG. 11, the disk 22 is in the form of a cylinder having a plurality of radially extending channels 22a which receive the liquid lithium 14b from the lithium channeling means 30. In this way, the disk 22 may rotate to create axially spaced apart spinning sheets of the liquid lithium 14b though which the proton beam 12a may be directed. In this embodiment, the first ground electrode 32c is again in the form of a beryllium foil, or grid, joined to its respective disk 22 coaxially with the lithium targets, and the second ground electrode 32c may form a portion of the target enclosure. Since the individual sheets of the liquid lithium 14b may not be practically formed as corresponding electrodes, two bias electrodes 32b are used to bridge all of the liquid sheets. The first biasing electrode 32b as shown in FIG. 11 can also be in the form of a beryllium foil, or grid, attached to a corresponding disk 22 with respective electrical insulators 34 being positioned between the adjacent stacked disks. The first biasing electrode 32b is suitably joined to the power supply 32a for biasing the electrode at a maximum positive DC potential such as plus 200 kV for example.

The second or downbeam biasing electrode 32b may be a relatively thick stationary member formed of beryllium for providing an effective stop for the proton beam 12a after it traverses the lithium sheets, and is suitably joined to the power supply 32a at the maximum negative potential of about minus 200 kV.

In this way, a suitable DC voltage potential is maintained axially across all of the lithium sheets 14b from the maximum positive potential before the first target sheet to the maximum negative potential after the last target sheet. In view of the voltage gradient provided between the two biasing electrodes, the voltage potential at each of the several lithium sheets 14b varies incrementally along the axial distance between the two biasing electrodes.

In both embodiments illustrated in FIGS. 8–11, the proton beam 12a first impacts a target at ground potential producing neutrons and loosing energy as it does. It then loses further energy due to the electric field between the ground foil and the first interior target, which is maintained at a positive potential of about 200 kV with respect to ground.

The proton beam then passes through the sequence of targets, and is reaccelerated by the electric fields between the sequential series of targets. In this example, the average energy lost by the beam is 50 keV each time it passes through a target. The target may either be dry such as beryllium, or wet such as liquid lithium, with or without the backing beryllium foil. The energy loss per target may be adjusted over a wide range depending on design considerations.

On the one hand, a small energy loss in each target would allow DISCOS to operate slightly above the neutron production threshold, generating a directed neutron beam in which the maximum energy of the neutrons is low. On the other hand, this would require a large number of targets, since the average energy loss per target would be in the preferred range of about 5–10 keV. By suitably varying the number of targets, the optimum number thereof may be determined.

It should be noted that the energy lost by the proton beam as it penetrates the first ground foil and is decelerated by the first target which is at the plus 200 kV, is returned during the reacceleration process since the last target in the sequence is at minus 200 kV. In effect, the target arrangement enables the beam to operate at a quasi-constant energy, with an integrated total energy input about twice the potential difference of the first target above ground.

The potential of the first target should preferably be in the range of about 200–300 kV so that the total energy used in the reacceleration process would be in the range of about 400–600 keV.

A significant issue for the reacceleration embodiments illustrated in FIGS. 8–11 is the magnitude of parasitic currents in the target assembly, and the possibility of electrical breakdown between electrodes and targets. Protons striking a foil, grid, or droplet will generate secondary electrons. The electrons will contribute to parasitic currents in the applied field, and may lead to an avalanche type of electric breakdown.

Positive ions on the order of 1 keV in energy typically generate about one secondary electron per impact on a solid or liquid surface. The yield of secondary electrons increases as the energy of the impacting ion increases at least in the range of a few keV. It thus appears likely that 2 MeV protons impacting a target foil or droplet will generate multiple secondary electrons that are ejected from the surface.

These secondary electrons will then be accelerated by the applied electric field, traveling in an opposite direction to the ions since the DC field direction is chosen to reaccelerate the ions in their direction of travel. Depending on the yield of secondary electrons, the resultant parasitic electron current may be significantly larger than the proton beam current.

It is therefore desirable to inhibit the passage of secondary electrons in DISCOS target assemblies for reducing the likelihood of electrical breakdown as well as reducing the parasitic currents. In accordance with additional embodiments of the present invention illustrated schematically in FIGS. 12–15, means are provided for applying an external magnetic field around the targets 14 to inhibit radiation induced parasitic electrical currents for restraining electrical breakdown.

By applying a magnetic field orthogonal to the direction of the applied electric field, the secondary electrons would gyrate in tight circles around magnetic field lines, and are prevented from traveling in the direction of the applied electric field. Using a magnetic field of a modest strength of about 0.2 Tesla or 2000 Gauss, a 100 eV electron would have a conventional radius of gyration, or Larmor radius, of only 150 microns. Lower energy electrons would have even smaller Larmor radii. As a result, secondary electrons will be effectively trapped by the applied magnetic field, and unable to impact adjacent target foils or droplets. This should completely eliminate secondary current and the possibility of electrical breakdown. The trapped electrons will move in helical orbits, drifting along the magnetic field lines until they encounter the rotating disk or the surrounding structure.

The magnetic field may be generated either by conductor windings or by permanent magnets in a suitable configuration. Several exemplary configurations are possible.

Figure 12:
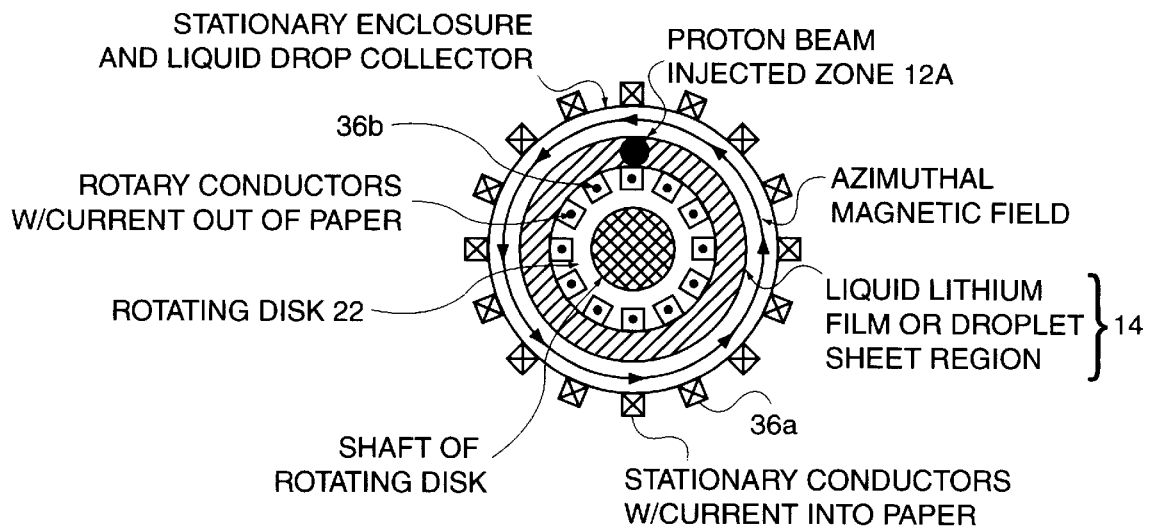
FIG. 12 is a schematic sectional view of one embodiment of an azimuthal magnetic field surrounding the multiple targets illustrated in FIG. 8.

In a first embodiment illustrated in FIG. 12, a purely azimuthal magnetic field is generated around the targets 14 by using coaxial current distribution. A plurality of circumferentially spaced apart, axially extending outer conductors 36a are suitably mounted in the stationary enclosure surrounding the targets 14, and a cooperating plurality of circumferentially spaced apart, axially extending inner conductors 36b are suitably mounted at the rim of the disks 22 below the targets 14. Electrical current from a suitable power supply is carried axially through the rotary inner conductors 36b and returns through the stationary outer conductors 36a in a series path for creating the azimuthal magnetic field in the region of the proton beam 12a.

Figure 13:
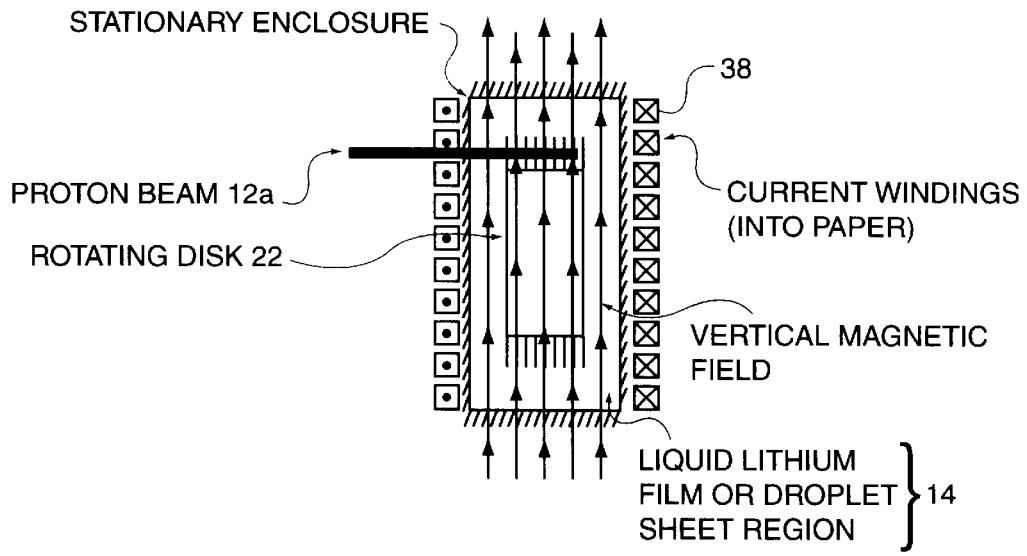
FIG. 13 is a schematic sectional view of a dipole magnetic field surrounding the multiple targets illustrated in FIG. 8 in accordance with another embodiment of the present invention.

FIG. 13 illustrates a second embodiment for effecting a dipole magnetic field vertically through the disk 22. A coil 38 of conductor windings is mounted in the stationary enclosure surrounding the disk 22 to generate a vertical magnetic field through which the disk rotates.

Figure 14:
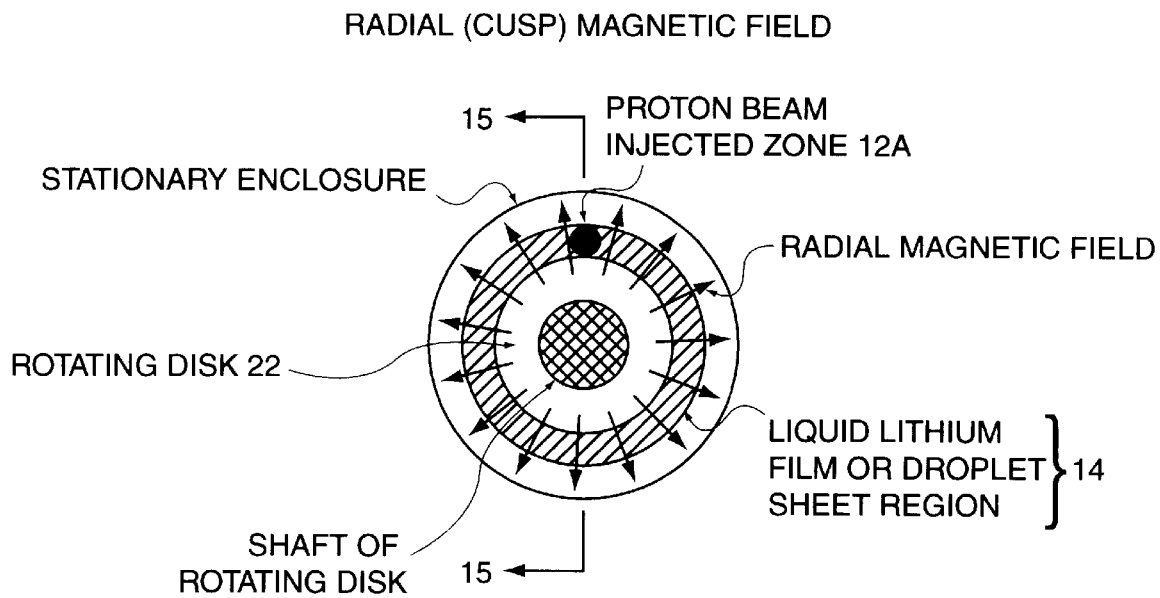
FIG. 14 is a schematic radial sectional view of a radial magnetic field surrounding the multiple targets illustrated in FIG. 8 in accordance with another embodiment of the present invention.
Figure 15:
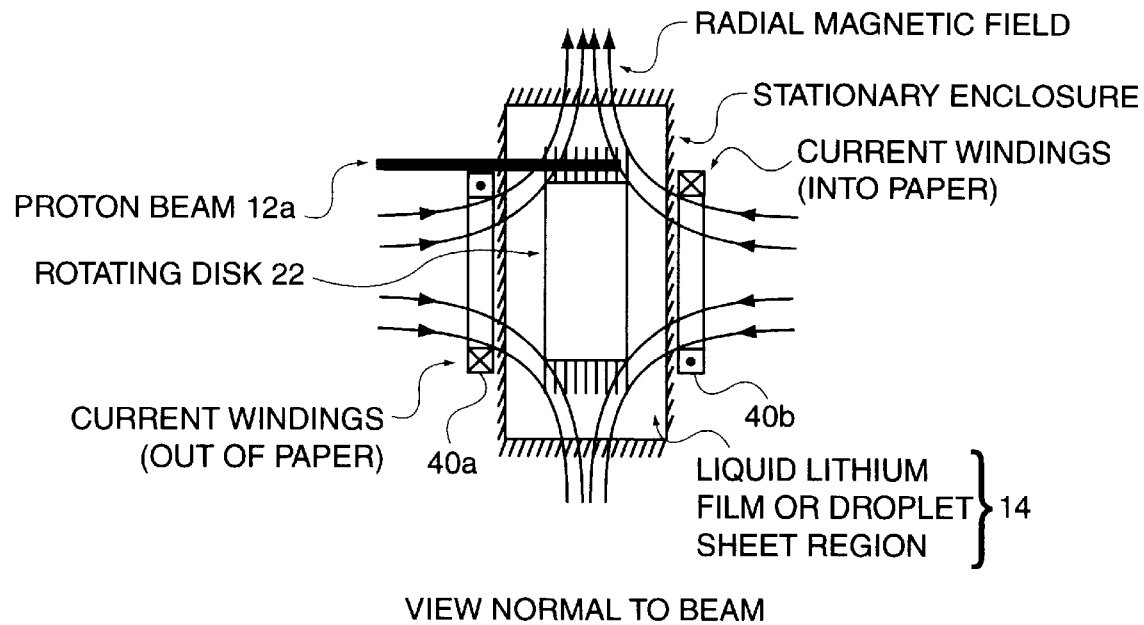
FIG. 15 is a schematic axial view through the embodiment illustrated in FIG. 14 and taken along line 15—15.

And, FIGS. 14 and 15 illustrate a third embodiment effecting a radial magnetic field. A pair of coil windings 40a,b are suitably fixedly mounted to the stationary enclosure surrounding the disk 22 coaxially with and on opposite axial sides thereof. The two coils 40a and 40b are suitably joined to a power supply for channeling current therethrough in opposite directions to each other. The resultant cusp field would be predominantly radial in the region of the targets 14.

In the azimuthal (FIG. 12) and radial (FIGS. 14–15) embodiments disclosed above, the generated magnetic field is azimuthally uniform with a constant magnitude at a given radius. In the dipole embodiment (FIG. 14), the magnetic field direction is not constant and does vary with azimuthal angle. However, the magnitude of the field is constant with azimuth.

The three magnetic geometry options disclosed have different current requirements. Based on a lithium target radius of about 10 centimeters, and a magnetic field strength of 2000 Gauss, the total current required for the azimuthal embodiment of FIG. 12 is on the order of 100,000 amp turns. For the radial embodiment of FIG. 14, the total current required is on the order of about 50,000 amp turns. And, for the dipole embodiment of FIG. 13, the total current is reduced to approximately 25,000 amp turns, based on a 10 centimeter long target region.

The DISCOS method enables the accelerator-target facility to operate with a beam energy only slightly above the threshold value for neutron production, resulting in an output beam of low-energy epithermal neutrons while achieving a high yield of neutrons per milliamp of proton beam current. The above-threshold value of the initial proton beam energy corresponds generally with the reduction in energy therein upon passing through the ultrathin target, on the order of one or two microns. In this way, the energy of the proton beam is minimized above the threshold for minimizing the energy of the resultant neutrons generated.

As indicated above, the desired epithermal energy range for conducting boron neutron capture therapy is about 1 eV–10 keV. And, epithermal neutrons have an energy up to about 100 keV. Although the DISCOS apparatus disclosed above can directly generate relatively low energy epithermal neutrons from proton beam interaction with the targets, the epithermal neutron spectrum is likely to include energies in the undesirable region between 10–100 keV, and possibly higher.

Accordingly, it is further desirable to condition the generated neutron beam at the outlet treatment port 20a illustrated in FIGS. 1 and 2 for providing primarily epithermal neutrons below about 10 keV, and with suitable neutron utilization efficiency. Neutron utilization efficiency is a conventional parameter proportional to the product of the neutron current at the treatment port and the area of the treatment port divided by the neutron generation rate at accelerator target 14. In previous accelerator-based neutron generator studies with lithium and beryllium targets, neutron utilization efficiency on the order of about $10^{-1}$ have been reported, but a substantially higher value thereof is required for a practical treatment facility to effect boron neutron capture therapy. For the neutron utilization efficiency on the order of $10^{-3}$, a proton beam current of about 100 milliamps is required, which is an impractically large value.

Accordingly, it is desirable to provide a neutron conditioning and transport design that can achieve a substantially greater neutron utilization efficiency for boron neutron capture therapy. With a neutron utilization efficiency of about $10^{-1}$, for example, the proton current for a useful accelerator-target source need only be about 1 milliamp. A new neutron conditioning/transport concept termed NIFTI is illustrated in an exemplary embodiment in FIG. 16, which is an acronym for Neutron Intensification by Filtered Transmission through Iron.

Figure 16:
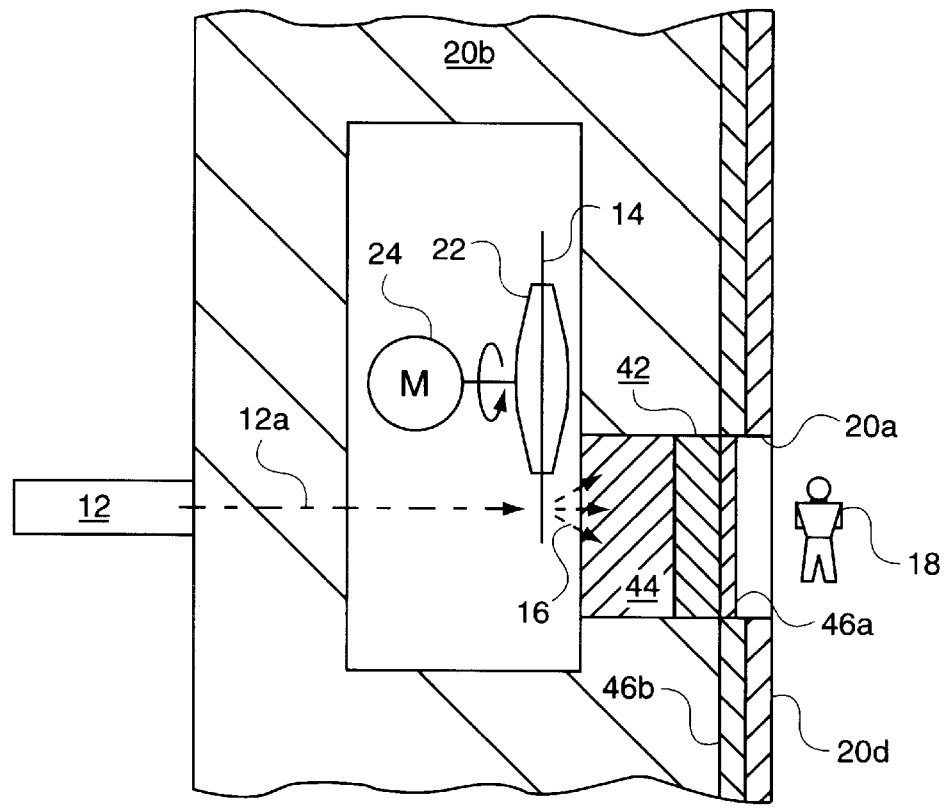
FIG. 16 is an enlarged partly sectional view of a portion of the apparatus illustrated in FIG. 1 showing a neutron scatterer and neutron filter disposed in turn between the rotary target and an outlet treatment port.

In FIG. 16, a neutron filter 42 in accordance with one embodiment of the present invention is interposed between the target 14 and the treatment port 20a and has a high-low step in scattering cross section at a specific step energy below about 100 keV for impeding neutron transmission therethrough at energies above the step energy, and permitting, without substantial degradation, neutron transmission therethrough at energies below the step energy. In the preferred embodiment, the neutron filter 42 is a suitably thick layer of primarily iron (Fe) which filters out unwanted high energy neutrons while letting neutrons of acceptable energy for treatment pass through almost unimpeded. Iron has a large window in its scattering cross section at a 24 keV step energy. Iron also has a low scattering cross section less than about 1 barn below the step energy, and above the step energy, iron has a substantially high scattering cross section of about 100 barns.

Accordingly, neutrons with energies above about 24 keV are strongly impeded from transmission through the neutron filter 42, while neutrons with energy below about 24 keV readily pass through the filter 42 relatively unimpeded.

In this way, by positioning the neutron filter 42 between the target 14 and the treatment port 20a in the embodiment illustrated in FIG. 16, any high energy neutrons in the output beam 16 above the 24 keV step energy are impeded from reaching the treatment port 20a, while the lower energy epithermal neutrons pass unimpeded thereto. The neutron filter 42 is most effective with the DISCOS apparatus 10 having a proton beam energy only slightly above the threshold required for neutron production. The resultant neutron spectrum is relatively low in energy, with a maximum value of about 100 keV or less. And, the neutron angular distribution is strongly non-isotropic.

In another embodiment described hereinbelow, the proton beam energy may have a greater excess above the threshold for generating the neutrons over a wider spectrum of energies, with a maximum value of hundreds of keV, and a more isotropic angular distribution. In this case, a suitable neutron scatterer 44 is interposed between the target 14 and the neutron filter 42 for substantially degrading the energy of the neutrons 16 so that they may be effectively filtered by the neutron filter 42.

The NIFTI process in accordance with the present invention provides an improved method for degrading neutron energy in shaping the epithermal spectrum. The NIFTI process can result in neutron utilization efficiencies on the order of about 5–10% which is substantially greater than the fractions of a single percent previously reported. The increased neutron utilization efficiency enables the use of much lower beam current requirements, on the order of a few milliamps, so that existing accelerator technology may be readily used for boron neutron capture therapy at reasonable cost.

Although the neutron filter 42 preferably includes iron for its filtering effectiveness, iron may be used with a secondary filtering material such as vanadium, titanium, magnesium, nickel, chromium, and manganese. Each of these materials has a corresponding characteristic window at different neutron energies and may be used in suitable combinations with iron to control the energy spectrum of the neutrons that pass through the filter 42.

Furthermore, some hydrogenous, energy downshifting material, either as a separate dispersoid, or as a partial metal hydride, may be incorporated in the filter 42 to more rapidly drop the energy of the neutrons so that they pass through the corresponding scattering window. The hydrogenic material may be in the form of small dispersed plastic beads or a layered structure of iron and plastic sheets, for example. The filter may consist of a suitable hydriding material such as iron-titanium, and the hydrogen may be present in a controlled concentration as $FeTiH_x$, where x would be adjusted to the value desired. Hydrogen is effective for accelerating the energy loss of the secondary neutron particles for reaching the desirable low epithermal range.

Two neutron transport geometries are possible for implementing NIFTI, i.e., open cavity geometry and closed solid geometry. FIG. 16 illustrates one form of the closed solid geometry wherein the neutron source or target 14, together with the iron filter 42 and neutron scatterer 44, if used, are substantially enclosed by a close fitting reflector 20b. Neutrons transmitted through the filter 42 at the treatment port 20a directly interact with the patient 18, while a portion of the neutrons that interact with the surrounding reflector 20b are scattered back into the treatment port 20a.

The closed solid geometry permits the neutron source to be located at the minimum possible distance from the patient, which acts to increase neutron utilization efficiency. However, the neutrons leaving the source that do not travel in the direction of the treatment port tend to be lost by diffusion, though a portion is scattered back toward the port.

In the open cavity geometry, the neutron source or target 14, and the filter 42 and scatterer 44, if used, are located in an open cavity as disclosed hereinbelow. The open cavity geometry collects and returns scattered neutrons back to the treatment port 20a to increase neutron utilization efficiency. However, since the source is located further away from the patient than is the case for the closed solid geometry, the increased distance tends to decrease neutron utilization efficiency.

In the exemplary embodiment illustrated in FIG. 16, the neutron scatterer 44 neutron filter 42 are aligned together between the target 14 and the treatment port 20a for in turn receiving the neutron beam 16. The neutron reflector 20b may be a suitable material such as lead or titanium. An optional, first absorber 46a may be interposed between the filter 42 and the treatment port 20a for absorbing neutrons having too low energy below the desired value, and may be formed of any suitable material such as $B_4C$. A second low energy neutron absorber 46b surrounds the first absorber 46a around the treatment port 20a and may be formed of a suitable material such as LiH. The forth shield 20d surrounding the treatment port 20d is preferably formed of a low energy neutron absorbing material, such as $B_4C$, to effectively reduce undesirable neutron leakage therethrough.

Figure 17:
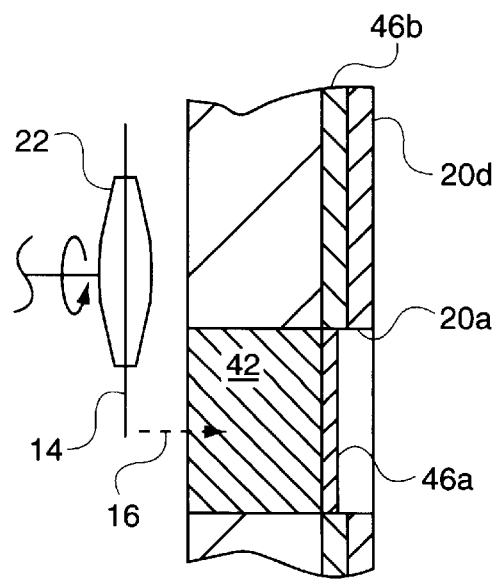
FIG. 17 is a schematic, partly sectional view like FIG. 16 in accordance with another embodiment of the present invention having solely the neutron filter between the rotary target and the outlet treatment port.

As indicated above, the neutron conditioner defined by the filter 42 alone, or in combination with the scatterer 44, is effective for conditioning the neutron beam 16 to pass only the desired low energy epithermal neutrons from the higher energy neutron source. When the neutron beam 16 generated from the target 14 has energies below about 100 keV, then solely the neutron filter 42 by itself may be used in the chamber 20 as illustrated schematically in FIG. 17. When the neutron beam 16 has energies greater than about 100 keV, the use of the filter 42 alone is not effective for inhibiting transmission of the high energy neutrons which will therefore pass therethrough unimpeded.

Accordingly, for accelerator targets which are either stationary or of the rotary DISCOS configuration and produce substantial amounts of higher energy epithermal neutrons greater than about 100 keV, the preferred neutron conditioner is a combination of both the neutron filter 42 and scatterer 44.

In the preferred embodiment, the neutron scatterer 44 comprises fluorine for its specific ability to inelastically degrade the high energy neutrons. Fluorine has a relatively high inelastic cross section, with a very low threshold energy for inelastic scattering of about 100 keV extending up to about 300 keV, with a maximum inelastic cross section of about 3.5 barns. Fluorine appears to be unique among elements in its low threshold energy for inelastic scattering and high value of inelastic cross section for effectively scattering neutrons above the 100 keV level. Most elements have threshold energies of at least 1 MeV and therefore would be ineffective when used in conjunction with the preferred neutron filter 42.

By positioning the neutron scatterer 44 adjacent to the neutron filter 42 to face the neutron source targets 14, the higher energy neutrons in the neutron beam 16 are firstly inelastically scattered for degrading their energy below the 100 keV limit of the iron neutron filter 42, and thereby allowing the neutron filter 42 to effectively operate and filter epithermal neutrons to the treatment port 20a.

In contrast to conventional moderators for boron neutron capture therapy, fluorine has the advantage of inelastically and efficiently scattering neutrons that are above 100 keV in energy, but do not continue to degrade them after they have been down scattered into the epithermal range for BNCT requiring only a few tens of keV. Degradation of neutron energy by inelastic scattering is preferable to degradation by a moderator, because the neutrons once degraded by inelastic collision stay relatively constant in energy rather than continuing to loose energy to the point where they are no longer useful for therapy. It is noted that the neutron energy after a typical inelastic scattering event in fluorine will be much lower than 100 keV.

The combination of the fluorine inelastic scatterer 44 and the iron neutron filter 42 provides an effective neutron conditioner which efficiently degrades neutron energy down to average values on the order of 10 to 20 keV which can be used effectively for therapy. This neutron conditioning may be effected with relatively thin layers of these materials so that the fraction of neutrons reaching the treatment port 20a is high.

Fluorine may be provided in various fluoride compounds, with the major advantage being that in fluorine, neutron energy degradation essentially ceases below 100 keV. In contrast, conventional moderators degrade energy continuously all the way down to thermal energy which is undesirable for use in conjunction with the neutron filter. Suitable fluoride compounds include $CF_2$, $PbF_2$, $BeF_2$, $VF_4$, $TuF_4$, $FeF_2$, $AlF_3$, $GaF_3$, and Teflon. These compounds may be used in various combinations. For example, FIG. 2 illustrates a neutron scatterer in two adjoining portions 44a and 44b, with the former providing a beryllium fluoride layer, and the latter providing a lead fluoride layer disposed in turn between the target 14 and the neutron filter 42.

Figure 18:
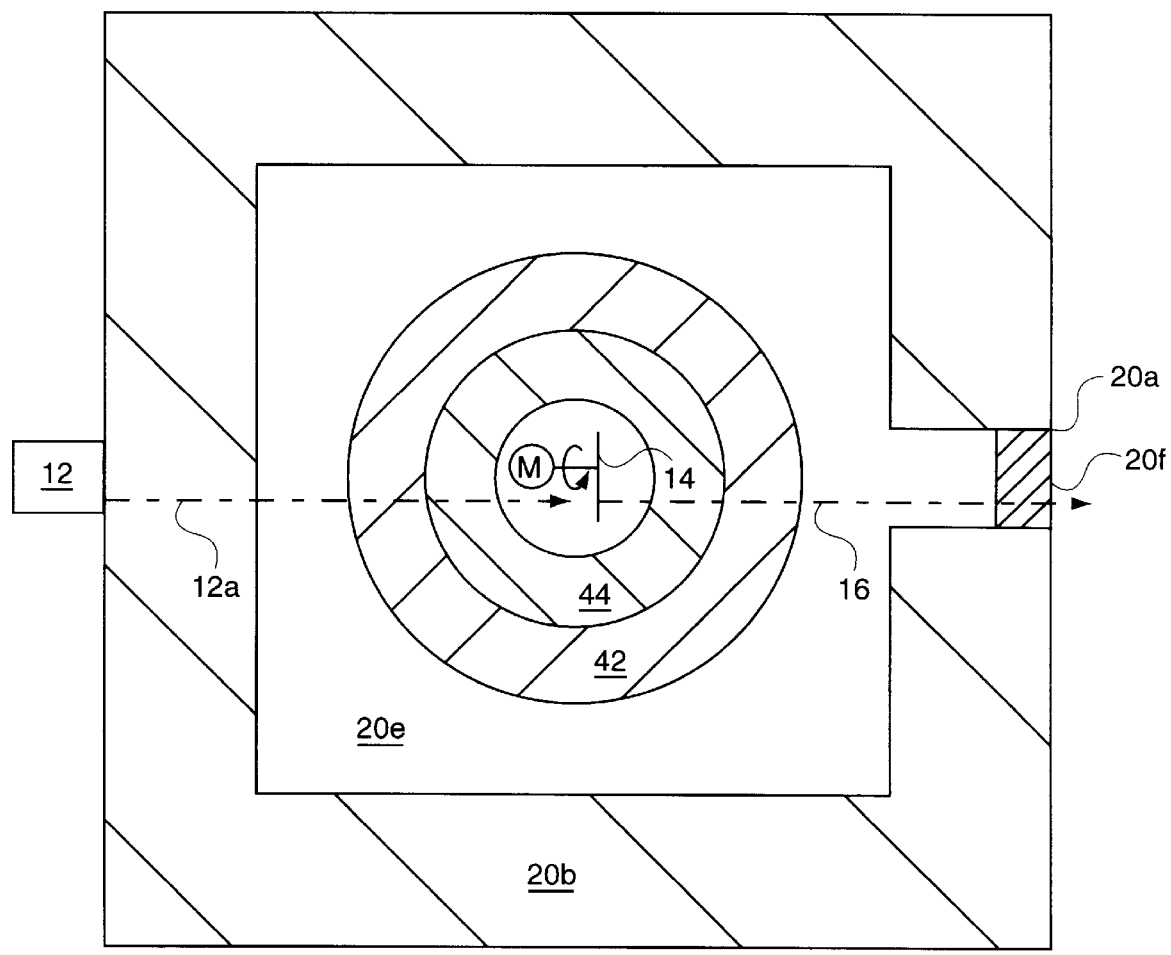
FIG. 18 is a partly sectional, schematic view of an open cavity embodiment of a neutron scatterer and neutron filter surrounding a neutron source in accordance with another embodiment of the present invention.

FIG. 18 illustrates schematically an exemplary open cavity NIFTI design. The target 14 is surrounded first by the neutron scatterer 44, if desired, and in turn is surrounded by the neutron filter 42 all located within an open cavity 20e surrounded by a suitably configured neutron reflector 20b. The proton beam 12a is suitably directed to the target 14 for generating the secondary neutrons therefrom. Neutrons transmitted through the iron filter 42 are scattered from the walls of the cavity 20e and finally escape through the treatment port 20a. The treatment port 20a may be an open window, or may incorporate a conventional gamma shield 20f to reduce unwanted radiation dose to the patient.

The NIFTI conditioner may be used to advantage with the DISCOS rotating target 14, or may be used with any suitably fixed target if desired. In either embodiment wherein a proton beam generates neutron particles from (p,n) reactions in a suitable target, the neutron filter 42 and scatterer 44 may provide enhanced conditioning of the neutrons for reducing their energy levels in a unique arrangement for producing relatively low epithermal neutrons on the order of 10 keV for boron neutron capture therapy.

DISCOS and NIFTI enable the efficient production of epithermal neutrons for boron neutron capture therapy utilizing a low current, low energy proton beam impacting a lithium target in the preferred embodiment. The NIFTI conditioner uses fluoride compounds such as lead or beryllium fluoride to efficiently degrade high energy neutrons from the lithium target to the lower energies required for the therapy. The fluoride compounds are in turn followed by an iron layer that strongly impedes the transmission of neutrons with energies above 24 keV. Lower energy neutrons readily pass through the iron filter, which has a deep window in its scattering cross section at 24 keV.

The DISCOS apparatus uses rapidly rotating, high "g" disks to create a series of thin, micron thick liquid lithium targets in the form of continuous films, or sheets, or droplets in a preferred embodiment through which the proton beam passes. The average energy lost by a proton as it passes through a single target is small and about 10 keV. Between the targets, the proton beam is reaccelerated by an applied DC electric field. The DISCOS apparatus enables the accelerator to operate with a beam energy only slightly above the threshold value for neutron production resulting in an output beam of low energy epithermal neutrons, while achieving a high yield of neutrons per milliamp of proton beam current.

A favorable output neutron energy spectrum for boron neutron capture therapy is provided with advantages including depth of penetration and ratio of tumor/healthy tissue dose that are comparable to those of current and proposed neutron therapy facilities. An effective amount of output neutron flux is achieved using a relatively low proton beam current on the order of about 5 milliamps which is an order of magnitude smaller than that proposed for published accelerator-based neutron therapy.

Although the invention has been described specifically with respect to boron neutron capture therapy and the use of a proton beam to liberate epithermal neutrons from a suitable target, the invention may also be used with different types of nuclear particles if desired.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims:

1. A method of generating low energy nuclear particles comprising:
   generating an input particle beam (12a) having an initial energy level above a threshold for generating said nuclear particles;
   rotating a target (14); and
   directing said input beam (12a) at said target (14) for undergoing nuclear reactions therein to generate secondary nuclear particles (16) and to correspondingly decrease energy of said input beam to about said threshold and further comprising:
   rotating a plurality of axially adjoining ones of said targets (14);
   directing said input beam (12a) in turn through said targets (14) to generate said secondary particles (16) and decrease energy of said input beam at each of said targets to about said threshold; and
   reaccelerating said input beam (12a) between succeeding ones of said targets to about said initial energy level prior to undergoing said nuclear reactions therein.

2. A method according to claim 1 further comprising applying a direct current voltage potential across said targets to reaccelerate said input beam therebetween.

3. A method according to claim 2 further comprising applying said voltage potential in incremental steps at each of said targets in turn.

4. A method according to claim 3 further comprising applying a magnetic field around said targets to inhibit radiation induced parasitic electrical currents for restraining electrical breakdown.

5. A method of generating low energy nuclear particles comprising:

generating an input particle beam (12a) having an initial energy level above a threshold for generating said nuclear particles;

rotating a target (14); and directing said input beam (12a) at said target (14) for undergoing nuclear reactions therein to generate secondary nuclear particles (16) and to correspondingly decrease energy of said input beam to about said threshold wherein:
said input beam is a proton particle beam;
said secondary nuclear particles are neutrons;
said target is lithium;
said threshold is about 1.88 MeV;
said initial energy level is less than about 2.2 MeV; and
said neutrons have an energy less than about 100 keV.

6. A method of generating low energy nuclear particles comprising:

generating an input particle beam (12a) having an initial energy level above a threshold for generating said nuclear particles;

rotating a target (14);

directing said input beam (12a) at said target (14) for undergoing nuclear reactions therein to generate secondary nuclear particles (16) and to correspondingly decrease energy of said input beam to about said threshold; and interposing with said target (14) a neutron filter (42) having a step in scattering cross section at a step energy below about 100 keV for respectively impeding and permitting neutron transmission therethrough at energies above and below said step energy.

7. A method according to claim 6 wherein said neutron filter (42) comprises iron and a secondary material selected from the group consisting of vanadium, titanium, magnesium, nickel, chromium, and manganese.

8. A method according to claim 7 wherein said neutron filter (42) further comprises hydrogen for accelerating energy loss of said secondary particles.

9. A method according to claim 7 further comprising interposing a neutron scatterer (44) between said target (14) and said neutron filter (42) for degrading said secondary particles above said 100 keV energy as opposed to there below.

10. A method according to claim 9 wherein said neutron scatterer (44) comprises fluorine having an inelastic cross section for inelastically scattering neutrons above said 100 keV energy.

11. An apparatus for generating low energy nuclear particles comprising:

a particle accelerator (12) for generating an input particle beam (12a) having an initial energy level above a threshold for generating said nuclear particles;

a target (14);

means (24) for rotating said target (14) and means (12b) for directing said input beam (12a) at said target (14) for undergoing nuclear reactions therein to generate secondary nuclear particles (16) and to correspondingly decrease energy of said input beam to about said threshold wherein said target comprises:
a plurality of arcuate foil segments (14a) fixedly joined to a perimeter of a disk (22), and said rotating means (24) are joined to said disk (22) to rotate said disk and foil segment (14a) attached thereto; and
means (30) for channeling a liquid to said disk perimeter to centrifugally form a liquid film on said foil segments for receiving said input beam.

12. An apparatus (10) for generating low energy nuclear particles comprising:

a particle accelerator (12) for generating an input beam (12a) having an initial energy level above a threshold for generating said nuclear particles;

a target (14);

means (24) for rotating said target (14);

means (12b) for directing said input beam (12a) at said target (14) for undergoing nuclear reactions therein to generate secondary nuclear particles (16) and to correspondingly decrease energy of said input beam to about said threshold;

wherein the target (14) further comprises a plurality of axially spaced apart targets (14) joined coaxially to said rotating means (24) for simultaneous rotation; and means (32) for reaccelerating said input beam (12a) between succeeding ones of said targets to about said initial energy level prior to undergoing said nuclear reactions therein.

13. An apparatus according to claim 12 wherein said reaccelerating means (32) comprise a plurality of biasing electrodes (32b) at different direct current voltage potential bridging said targets (14) to reaccelerate said input beam therebetween.

14. An apparatus according to claim 13 wherein said reaccelerating means (32) further comprise a power supply (32a) operatively joined to each of said targets (14) for applying incremental voltage potential steps thereat in turn.

15. An apparatus according to claim 14 further comprising means (36–40) for applying a magnetic field around said targets (14) to inhibit radiation induced parasitic electrical current for restraining electrical breakdown.

16. An apparatus for generating low energy nuclear particles comprising:

a particle accelerator (12) for generating an input particle beam (12a) having an initial energy level above a threshold for generating said nuclear particles;

a target (14);

means (24) for rotating said target (14); and means (12b) for directing said input beam (12a) at said target (14) for undergoing nuclear reactions therein to generate secondary nuclear particles (16) and to correspondingly decrease energy of said input beam to about said threshold wherein:
said input beam is a proton particle beam;
said secondary nuclear particles are neutrons;
said target is a lithium film less than about 2 microns thick;
said threshold is about 1.88 MeV;
said initial energy level is less than about 2.2 MeV; and
said neutrons have an energy less than about 100 keV.

17. An apparatus for generating low energy nuclear particles comprising:

a particle accelerator (12) for generating an input particle beam (12a) having an initial energy level above a threshold for generating said nuclear particles;

a target (14);

means (24) for rotating said target (14); and means (12b) for directing said input beam (12a) at said target (14) for undergoing nuclear reactions therein to generate secondary nuclear particles (16) and to correspondingly decrease energy of said input beam to about said threshold comprising:
a neutron filter (42) interposed with said target (14) and having a step in scattering cross section at a step energy at below about 100 keV for respectively impeding and permitting neutron transmission therethrough at energies above and below said step energy.

18. An apparatus according to claim 17 wherein said neutron filter (42) comprises iron and a secondary material selected from the group consisting of vanadium, titanium, magnesium, nickel, chromium, and manganese.

19. An apparatus according to claim 18 wherein said neutron filter (42) further comprises hydrogen for accelerating energy loss of said secondary particles.

20. An apparatus according to claim 18 further comprising a neutron scatterer (44) interposed between said target (14) and said neutron filter (42) for degrading said secondary particles above said 100 keV energy as opposed to therebelow.

21. An apparatus according to claim 20 wherein said neutron scatterer (44) comprises fluorine having an inelastic cross section for inelastically scattering neutrons above said 100 keV energy.

22. A conditioner according to claim 17 wherein said neutron filter (42) comprises iron and a secondary material selected from the group consisting of vanadium, titanium, magnesium, nickel, chromium, and manganese.

23. A conditioner according to claim 22 wherein said neutron filter (42) further comprises hydrogen for accelerating energy loss of said secondary particles.

24. A conditioner according to claim 22 further comprising:
a neutron scatterer (44) disposed adjacent to said neutron filter (42) to face said neutron source for degrading said secondary particles above said 100 keV energy as opposed to therebelow.

25. A conditioner according to claim 24 wherein said neutron scatterer (44) comprises fluorine having an inelastic cross section for inelastically scattering neutrons above said 100 keV energy.

* * * * *